(12) United States Patent
Roelver et al.

(10) Patent No.: US 9,423,377 B2
(45) Date of Patent: Aug. 23, 2016

(54) DEVICE FOR DETECTING AT LEAST ONE GASEOUS ANALYTE AND METHOD FOR THE PRODUCTION THEREOF

(71) Applicant: Robert Bosch GmbH, Stuttgart (DE)

(72) Inventors: Robert Roelver, Calw-Stammheim (DE); Daniel Pantel, Ditzingen (DE); Stefan Henneck, Leonberg (DE)

(73) Assignee: Robert Bosch GmbH, Stuttgart, DE (US)

( * ) Notice: Subject to any disclaimer, the term of this patent is extended or adjusted under 35 U.S.C. 154(b) by 0 days.

(21) Appl. No.: 14/945,211

(22) Filed: Nov. 18, 2015

(65) Prior Publication Data
US 2016/0146752 A1    May 26, 2016

(30) Foreign Application Priority Data
Nov. 21, 2014 (DE) .......................... 10 2014 223 778

(51) Int. Cl.
| | |
|---|---|
| *H01L 21/00* | (2006.01) |
| *G01N 27/416* | (2006.01) |
| *G01N 27/407* | (2006.01) |
| *H01L 21/62* | (2006.01) |
| *G01N 27/414* | (2006.01) |

(52) U.S. Cl.
CPC ........ *G01N 27/4166* (2013.01); *G01N 27/407* (2013.01); *G01N 27/4077* (2013.01); *H01L 21/62* (2013.01); *G01N 27/4143* (2013.01)

(58) Field of Classification Search
None
See application file for complete search history.

(56) References Cited

U.S. PATENT DOCUMENTS

| | | | | |
|---|---|---|---|---|
| 6,068,747 A | * | 5/2000 | Tojo ..................... | G01N 27/417 204/424 |
| 6,165,336 A | * | 12/2000 | Maki .................. | G01N 27/4074 204/415 |
| 2005/0263396 A1 | * | 12/2005 | Naito ................. | G01N 27/4071 204/424 |
| 2012/0323466 A1 | * | 12/2012 | Iwazaki .............. | F02D 41/0085 701/104 |
| 2014/0318961 A1 | * | 10/2014 | Huang ................. | G01N 27/407 204/424 |
| 2016/0047774 A1 | * | 2/2016 | Teysseyre .......... | G01N 27/4065 205/775 |

FOREIGN PATENT DOCUMENTS

| | | |
|---|---|---|
| DE | 10 2009 000 820 A1 | 8/2010 |
| DE | 10 2012 201 304 A1 | 8/2013 |

* cited by examiner

*Primary Examiner* — Angel Roman
(74) *Attorney, Agent, or Firm* — Maginot, Moore & Beck LLP

(57) ABSTRACT

A device for detecting at least one gaseous analyte comprises a detection section including a semiconductor substrate and at least one sensor element, which is arranged on the semiconductor substrate. The at least one sensor element includes two electrodes and a solid electrolyte layer arranged between the electrodes. The device also comprises a protective cap configured to cover the at least one sensor element, and at least one temperature-control unit configured for temperature control of the protective cap. The at least one temperature-control unit is arranged on the protective cap. The protective cap is formed from a semiconductor material. The device further comprises a diffusion section having a plurality of passage openings for the gaseous analyte arranged at least in a partial section of the protective cap.

10 Claims, 4 Drawing Sheets

DEVICE FOR DETECTING AT LEAST ONE GASEOUS ANALYTE AND METHOD FOR THE PRODUCTION THEREOF

This application claims priority under 35 U.S.C. §119 to patent application no. DE 10 2014 223 778.5, filed on Nov. 21, 2014 in Germany, the disclosure of which is incorporated herein by reference in its entirety.

The present disclosure relates to a device for detecting at least one gaseous analyte and to a method for producing a device for detecting at least one gaseous analyte, in particular for a use for an exhaust gas sensor system or the like.

BACKGROUND

A so-called lambda measurement, for example, by ceramic lambda sensors, which can frequently be implemented in thick-film technology from ceramics based on zirconium oxide, can be performed for measuring a residual oxygen fraction in exhaust gases of internal combustion engines and for feedback to an engine controller.

DE 10 2012 201 304 D1 discloses a micromechanical solid electrolyte sensor device and a corresponding production method.

SUMMARY

Against this background, using the approach presented here, a device for detecting at least one gaseous analyte and a method for producing a device for detecting at least one gaseous analyte are provided according to the main claims. Advantageous embodiments result from the respective dependent claims and the following description.

According to embodiments of the present disclosure, a micro-electrochemical sensor element having heated protective cap wafer or a gas-permeable, heatable protective cap, which is manufactured in micromechanics, made of a semiconductor material, for example, silicon, can be provided for a sensor chip. Therefore, for example, a protective cap for a gas sensor for detecting at least one gaseous analyte in a measurement medium can be provided, wherein the protective cap can enable access of the gaseous analyte to a sensor element of the gas sensor and can keep undesired materials of the measurement medium away from the sensor element.

According to embodiments of the present disclosure, in particular a porous, heated semiconductor protective cap made of, for example, silicon can advantageously be used on a micro-electrochemical sensor chip, to protect gas sensor elements by way of thermophoresis and active filtering of larger particles from soot deposits or from contaminants and deposits. In short, gas permeability and particle filter action can be achieved by way of a semiconductor protective cap arranged above a gas sensor element. Particles deposited in the protective cap or filter cap can be burned off in operation by active heating to greater than 800° C., for example, so that clogging of the filter cap can be prevented. Additional protection from particle deposits by way of thermophoresis can be provided by active heating, if a temperature of the protective cap is greater than an immediate surroundings temperature. Thus, sooting and poisoning of the sensor by soot burnoff residues or oil ashes can be prevented and reliable operation can be enabled over a sufficiently long service life. For example, by means of a sensor having such a protective cap, measurement of a residual oxygen fraction in exhaust gases of internal combustion engines and feedback of measured values to an engine controller, minimization of pollutants, for example, nitrogen oxides in exhaust gases can be improved. By means of suitable assembly, packaging, and housing technology, long-term stability and reliable operation of such a micro-electrochemical sensor can be improved. An improvement of the long-term stability can be achieved in the case of use of a gas-permeable, heatable semiconductor protective cap, which is manufactured in micromechanics, in particular by avoiding soot deposits and possible water hammer, by protection from poisoning, from mechanical stresses, from excessively high temperatures, etc. Furthermore, multiple compact sensor elements can also be integrated in one sensor housing in a simple manner.

In other words, in particular a miniaturized solid electrolyte gas sensor or micro-electrochemical gas sensor or MFCS (microelectronic chemical sensor) can be provided, which can be manufactured by way of the use of micromechanical methods and processes. Such a miniaturized solid electrolyte gas sensor can enable a reduction of a sensor element size and also a thickness reduction of an active solid electrolyte layer and, in addition to a reduced structural space as a result of reduced volume or ceramic volume, can offer still further advantages, for example, rapid operational readiness and lower required heating power. Therefore, a temperature which is required for the sensor operation of the gas sensor, which is used as a lambda sensor, for example, can be achieved by active heating after activation with minimized delay time and with reduced power consumption.

The gas sensor, which is used as a lambda sensor, for example, in the exhaust gas stream can have an optimum suitability for such a usage location, to protect a sensor element and required peripheral electrical connections from stresses such as corrosive exhaust gas, soot accumulations, high temperatures, and mechanical stresses. In this case, in particular dimensioning a sensor surface to be so large that individual, local soot deposits do not immediately result in sensor failure can be avoided. Sensor poisoning by corrosive exhaust gas components can be prevented by the protective cap. A reduction of dimensions of such a gas sensor can enable integration of further active sensor components, for example, in a lambda sensor housing, for example, a sensor element for additional monitoring of a nitrogen oxide concentration. Since assembly and packaging technology in the exhaust gas sensor system field can make up a large fraction of the total production costs, if a gas sensor having such a protective troop is used, it is possible to provide both functional advantages and also cost advantages as a result of the expandability.

A device for detecting at least one gaseous analyte is proposed, wherein the device comprises the following features:

a detection section, which comprises a semiconductor substrate and at least one sensor element, which is arranged on the semiconductor substrate, having two electrodes and a solid electrolyte layer arranged between the electrodes; and a protective cap for covering the at least one sensor element, wherein at least one temperature-control unit for temperature control of the protective cap is arranged on the protective cap, wherein the protective cap is formed from a semiconductor material, wherein a diffusion section having a plurality of passage openings for the gaseous analyte is arranged at least in a partial section of the protective cap.

The device can be designed to execute a qualitative detection and additionally or alternatively a quantitative detection of the gaseous analyte. In this case, the device can be able to be arranged in a measurement medium, wherein the measurement medium can comprise the at least one gaseous analyte. The detection section and additionally or alternatively the at least one sensor element can be embodied as a microelectronic chemical sensor. The detection section and the protective cap can be integrally joined with one another. The protective cap can be formed from silicon in particular.

According to one embodiment, the passage openings can have main axes of extension, which extend in parallel to one another within a tolerance range. In this case, the passage openings can have a diameter which is adapted to a molecule size of the at least one gaseous analyte. The passage openings can therefore be manufactured by means of a microprocessing process. In particular, the passage openings can have a diameter which is greater than a molecule size of the at least one gaseous analyte. In this case, the passage openings can have a diameter which is smaller than a diameter of contaminant particles in a measurement medium. Such an embodiment offers the advantage that suitably dimensioned passage openings can be provided both to reliably enable access of analytes to the sensor element and also to reliably prevent contaminants.

The protective cap can also have a lesser thickness inside the diffusion section than outside the diffusion section. The protective cap can therefore have a first thickness inside the diffusion section and can have a second thickness, which is greater than the first thickness, outside the diffusion section. Such an embodiment offers the advantage that access of a gaseous analyte to the at least one sensor element can be made easier, wherein a reaction time of the device with respect to a gaseous analyte can additionally be shortened. A heating power for reaching a soot burnoff temperature, for example, greater than 800° C., can therefore be reduced, expenditure for generating the gas-permeable passage openings can be minimized, and a connection of protective cap and detection section can be made easier.

Furthermore, the protective cap can be able to be formed or can be formed in a manner adapted to at least one parameter of usage surroundings of the device with respect to an area of the diffusion section and additionally or alternatively a volume which can be enclosed between the detection section and the protective cap, and in which the at least one sensor element is arranged. The at least one parameter of the usage surroundings of the device can comprise a composition, temperature, flow properties, etc. of the measurement medium and/or the like. In the case of a measurement medium having strongly contaminating action, for example, the area of the diffusion section can be made larger than in a case having a measurement medium having a less contaminating effect. The volume which can be enclosed or enclosure volume can be able to be formed or dimensioned in a manner adapted in dependence on the at least one gaseous analyte and additionally or alternatively on the measurement medium. Such an embodiment offers the advantage that more reliable access of a gaseous analyte can also be implemented in the long term by an area enlargement of the diffusion section. Furthermore, by adapting the enclosure volume, a reaction time or dynamic response of the at least one sensor element can be adapted suitably to usage conditions.

In addition, the at least one temperature-control unit can be connectable or connected in an electrically conductive manner to the detection section by means of at least one contact unit. In this case, the at least one temperature-control unit can be arranged adjacent to the diffusion section and additionally or alternatively at least partially inside the diffusion section. Such an embodiment offers the advantage that a potential accumulation of contaminants, in particular in the region of the diffusion section, can also be removed by thermophoresis or pyrolysis.

In particular, the at least one temperature-control unit can be formed from a metal. In this case, an insulator layer made of an electrically insulating material can be arranged between the at least one temperature-control unit and the protective cap. For example, in this case the temperature-control unit can be formed from platinum or a noble metal. Such an embodiment offers the advantage that such a temperature-control unit can be produced in a noncomplex manner on the protective cap and can be electrically insulated from a semiconductor material of the protective cap in a simple manner. The protective cap can therefore be heated effectively and efficiently.

A method for producing a device for detecting at least one gaseous analyte is also proposed, wherein the method comprises the following steps:

providing a detection section, which comprises a semiconductor substrate and at least one sensor element, which is arranged on the semiconductor substrate, having two electrodes and a solid electrolyte layer arranged between the electrodes, and a protective cap formed from a semiconductor material;

processing the protective cap, to arrange at least one temperature-control unit for temperature control of the protective cap on the protective cap and to create a diffusion section having a plurality of passage openings for the gaseous analyte at least in a partial section of the protective cap; and applying the protective cap to the detection section to cover the at least one sensor element.

An embodiment of the abovementioned device for detection is advantageously producible by execution of the method for production. The steps of the method can be carried out using micromechanical processes.

According to one embodiment, in the step of processing, a thickness of the protective cap within the diffusion section can be reduced to a lesser thickness than outside the diffusion section. A micromechanical cutting process can be executed for this purpose in the step of processing. Such an embodiment offers the advantage that a reaction speed or response behavior of the at least one sensor element of the device can be improved, in that access of a gaseous analyte to the at least one sensor element is made easier.

In the step of processing, the plurality of passage openings in the diffusion section of the protective cap can also be manufactured by means of at least one micromechanical process. The at least one micromechanical process can comprise etching and additionally or alternatively laser drilling for this purpose. Such an embodiment offers the advantage that the passage openings can be created accurately for a specification in an exact manner with respect to the dimensions thereof, to provide a defined diffusion barrier in the protective cap.

Furthermore, in the step of application, the at least one temperature-control unit can be connected in an electrically conductive manner to the detection section by means of at least one contact unit. In this case, the at least one temperature-control unit can be connected in an electrically conductive manner by means of the at least one contact unit to an electrical line arranged in or on the detection section. In particular, the contact unit can comprise a through contact or the like. Such an embodiment offers the advantage that additional external electrical terminal points for the at least one temperature-control unit can be avoided in the device.

BRIEF DESCRIPTION OF THE DRAWINGS

The approach proposed here will be explained in greater detail by way of example hereafter on the basis of the appended drawings. In the figures.

DETAILED DESCRIPTION

In the following description of advantageous exemplary embodiments of the present disclosure, identical or similar reference signs are used for the similarly acting elements shown in the various figures, wherein a repeated description of these elements is omitted.

Figure 1:
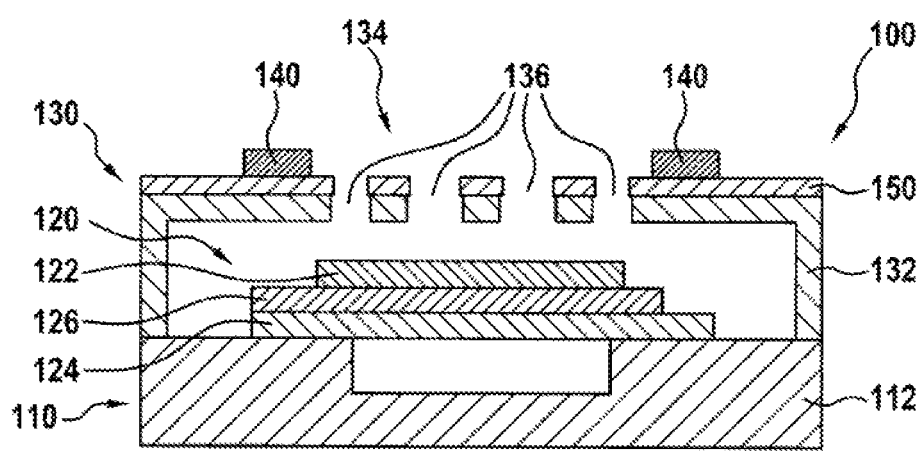
FIG. 1 shows a schematic sectional view of a detection device according to one exemplary embodiment of the present disclosure.

FIG. 1 shows a schematic sectional view of a detection device 100 according to one exemplary embodiment of the present disclosure. The detection device 100 is a device for detecting at least one gaseous analyte. In other words, the detection device 100 is designed to detect at least one gaseous analyte. In particular, the detection device 100 is designed in this case to qualitatively and/or quantitatively determine or detect the at least one gaseous analyte. The detection device 100 is embodied for this purpose as a solid electrolyte gas sensor or micro-electrochemical gas sensor, wherein the detection device 100 can be arranged, for example, in a measurement medium, which comprises the at least one gaseous analyte. The measurement medium includes, for example, exhaust gases of an internal combustion engine, in particular of a motor vehicle.

The detection device 100 comprises a detection section 110. The detection section 110 comprises a semiconductor substrate 112 or a wafer or sensor wafer in the form of a circuit board or printed circuit board. According to the exemplary embodiment of the present disclosure shown in FIG. 1, the detection section 110 has, for example, only one sensor element 120, which is arranged on the semiconductor substrate 112. The sensor element 120 is arranged for this purpose spanning a cavity formed in the semiconductor substrate 112 and applied to the semiconductor substrate 112.

The sensor element 120 comprises a first electrode 122, a second electrode 124, and a solid electrolyte layer 126. In this case, the solid electrolyte layer 126 is arranged between the first electrode 122 and the second electrode 124. The first electrode 122 and the second electrode 124 are embodied as platinum electrodes or formed from platinum (Pt) according to the exemplary embodiment of the present disclosure shown in FIG. 1, wherein the solid electrolyte layer 126 is formed from yttrium-oxide-stabilized zirconium oxide (YSZ). The sensor element 120 is therefore designed to carry out the actual detection of the at least one gaseous analyte, in particular oxygen.

The detection device 100 furthermore comprises a protective cap 130. The protective cap 130 is formed from a semiconductor material 132. The semiconductor material 132 comprises for this purpose a semiconductor substrate or a wafer or cap wafer in the form of a semiconductor body.

In this case, the protective cap 130 according to the exemplary embodiment of the present disclosure shown in FIG. 1 has a cross-sectional profile in the form of a polygonal shell or a U-shaped polygon. The protective cap 130 is designed to cover or span the sensor element 120 of the detection section 110. In this case, the protective cap 130 is applied to the detection section 110. More precisely, the protective cap 130 is integrally joined to the semiconductor substrate 112 of the detection section 110. In particular, the protective cap 130 is designed to enable access of the at least one gaseous analyte to the sensor element 120 and to protect the sensor element 120 from particles, contaminant materials, etc. of the measurement medium.

A diffusion section 134 is arranged in the protective cap 130 or the semiconductor material 132. According to the exemplary embodiment of the present disclosure shown in FIG. 1, the diffusion section 134 is formed in a partial section of the protective cap 130. In this case, the diffusion section 134 is arranged adjacent to the sensor element 120 of the detection section 110. An intermediate space extends for this purpose between the diffusion section 134 and the sensor element 120. Furthermore, the protective cap 130 or the semiconductor material 132 of the protective cap 130 has a lesser thickness in the region of the diffusion section 134 than outside the diffusion section 134.

The diffusion section 134 has a plurality of passage openings 136 or pores. The passage openings 136 are formed in the region of the diffusion section 134 in the protective cap 130 or the semiconductor material 132 of the protective cap 130. In this case, the passage openings 136 are created by means of micromechanical processes. The passage openings 136 are designed to enable a passage of the at least one gaseous analyte from a side of the protective cap 130 facing toward the measurement medium to a side of the protective cap 130 facing toward the sensor element 120.

According to the exemplary embodiment of the present disclosure shown in FIG. 1, the passage openings 136 have main axes of extension extending in parallel to one another within a tolerance range. In this case, the passage openings 136 also have a diameter which is adapted to a molecule size of the at least one gaseous analyte.

In addition, the detection device 100 according to the exemplary embodiment of the present disclosure shown in FIG. 1 as an example only has one temperature-control unit 140. The temperature-control unit 140 is arranged in this case on the protective cap 130. More precisely, the temperature-control unit 140 is arranged adjacent to the diffusion portion 134 of the protective cap 130. The temperature-control unit 140 is arranged on a side of the protective cap 130 facing toward the measurement medium or facing away from the sensor element 120. The temperature-control unit 140 is designed to control the temperature of the protective cap 130. In this case, the temperature-control unit 140 according to the exemplary embodiment of the present disclosure shown in FIG. 1 is embodied as a platinum heater solely as an example. The temperature-control unit 140 can optionally also be formed from another metal.

According to one exemplary embodiment, an insulator layer 150 made of an electrically insulating material is arranged between the temperature-control unit 140 and the protective cap 130 or the semiconductor material 132 of the protective cap 130. The insulator layer 150 is designed to electrically insulate the temperature-control unit 140 from the semiconductor material 132 of the protective cap 130.

According to one exemplary embodiment, the protective cap 130 can be or become formed in a manner adapted to at least one parameter of usage surroundings of the detection device 100 with respect to an area of the diffusion section 134 and additionally or alternatively with respect to a volume enclosed between the detection section 110 and the protective cap 130 or an enclosure volume, in which the sensor element 120 is arranged. According to one exemplary embodiment, the temperature-control unit 140 can also be or become connected in an electrically conductive manner to the detection section 110 by means of at least one contact unit.

In other words, FIG. 1 shows a basic structure of the detection device 100 or a gas sensor. To be able to omit external reference air access, in operation of the detection device 100, the cavity or reference air cavity in the detection section 110, which is spanned by the sensor element 120, can be pumped full of oxygen by applying a pump current between the two electrodes 122 and 124 or platinum contacts. An oxygen reference value having elevated oxygen concentration can thus be obtained, which can then be calibrated with the oxygen partial pressure in the exhaust gas via a Nernst voltage between the electrodes 122 and 124. Since a sensor area of the detection device 100 can have membrane areas between 10 μm and several hundred micrometers for this purpose, a deposit of gas-blocking solids on the sensor element 120 can be prevented by means of the porous protective cap 130 made of silicon.

FIGS. 2A to 2E show schematic sectional views of at least parts of the detection device from FIG. 1 in different production states. In other words, FIGS. 2A to 2E show a possible process flow during a production of an MECS sensor element provided with a porous, heated protective cap.

Figure 2A:
FIGS. 2A to 2E show schematic sectional views of the detection device from FIG. 1 in different production states.

In this case, FIG. 2A shows the semiconductor material 132 or the cap wafer or silicon wafer for the protective cap in a starting state.

Figure 2B:
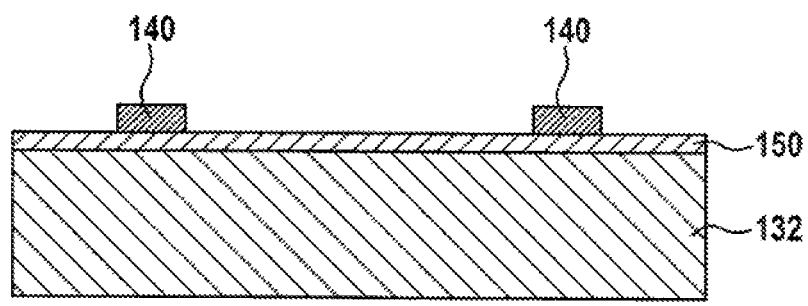

FIG. 2B shows the semiconductor material 132 for the protective cap from FIG. 2A with temperature-control unit 140, which is applied to the semiconductor material 132, and insulator layer 150. Therefore, FIG. 2B shows the detection device in a partially produced state. To avoid material fractures in the semiconductor material 132 during production of the protective cap, for example, firstly the temperature-control unit 140 and the insulator layer 150 are created. The temperature-control unit 140 is embodied as exhaust-gas-resistant and temperature-resistant and is formed, for example, from platinum or alternatively from gold. For the electrical insulation of the temperature-control unit 140 or the heater from the semiconductor material 132 or semiconducting substrate, the insulator layer 150 or an electrical insulation layer is arranged between the temperature-control unit 140 and the semiconductor material 132. The insulator layer 150 is created, for example, by thermal oxidation or plasma-enhanced chemical vapor deposition (PECVD) of silicon dioxide ($SiO_2$) or silicon nitride (SiN). For example, sputtering or atomic layer deposition (ALD) are suitable for the deposition of the metal layer for the temperature-control unit 140, shadow masks or lithographic methods are usable for the structure definition. Alternatively to the mentioned deposition and structuring methods, it is possible to create the temperature-control unit 140 via screen printing of pastes containing noble metals on the semiconductor material 132.

Figure 2C:
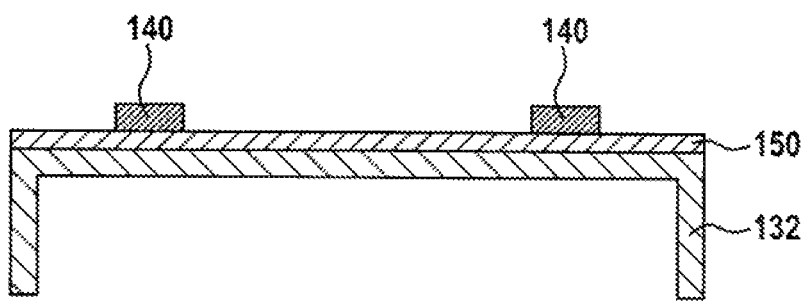

FIG. 2C shows the semiconductor material 132 for the protective cap with the temperature-control unit 140 and the insulator layer 150 from FIG. 2B in a further processed state. In this case, the semiconductor material 132 is partially removed from a side facing away from the temperature-control unit 140 and the insulator layer 150 to create the cross-sectional profile, which is in the form of a polygonal shell or U-shaped polygon, of the semiconductor material 132 of the protective cap. In other words, the semiconductor material 132 is thinned out or reduced with respect to a material thickness at least in a region or filter region which is provided for the diffusion section, i.e., in the region of a heated and gas-permeable section of the protective cap. This thinning out can be performed, for example, by reactive ion etching (RIE) or dry etching or wet-chemical etching, in particular using KOH.

Figure 2D:
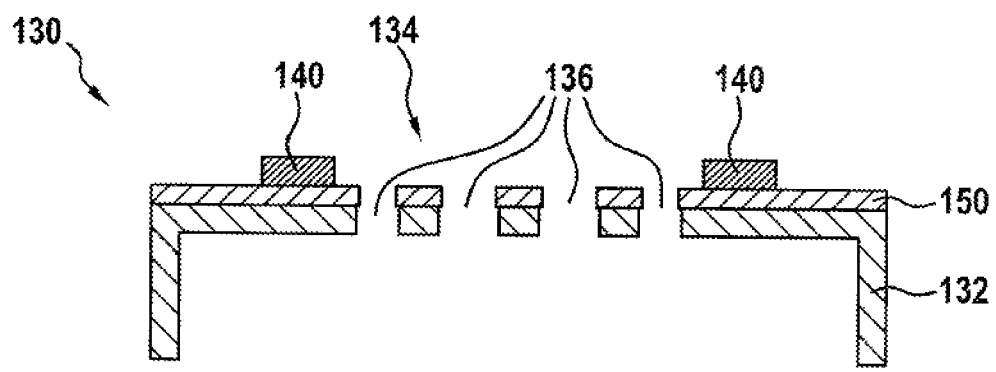

FIG. 2D shows the protective cap 130 in a finished state. In other words, FIG. 2D shows the semiconductor material 132 for the protective cap 130 with the temperature-control unit 140 and the insulator layer 150 from FIG. 2C in a still further processed state having the plurality of passage openings 136 formed in the diffusion section 134. In this case, the passage openings 136 or pores can be created by etching or laser drilling. Gas permeability and a particle filter action of the protective cap 130 can thus be achieved. Etching methods usable for this purpose comprise deep reactive ion etching (DRIE), wet-chemical KOH etching of pores previously defined by lithography, for example, etc. Alternatively, laser drilling can also be applied for forming the passage openings 136 or for creating pores.

Figure 2E:
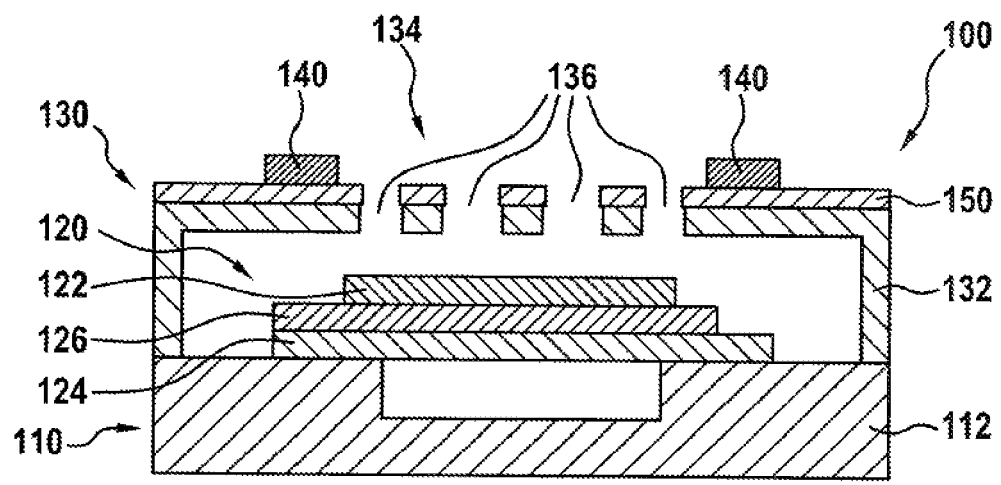

FIG. 2E shows the detection device 100 in a micromechanically finish-processed state. More precisely, FIG. 2E shows the protective cap 130 from FIG. 2D in a state connected to the detection section 110. Therefore, the illustration in FIG. 2E corresponds to the illustration in FIG. 1. After completion of the protective cap 130, it is connected by means of a suitable bonding method to the semiconductor substrate 112 or sensor wafer of the detection section 110. For wafer-wafer connections which have long-term stability and temperature stability, for example, anodic silicon-silicon bonding can be used.

It is to be noted with reference to FIGS. 2A to 2E that a diameter of the passage openings 136 or a pore size and the enclosure volume between the protective cap 130 and the detection section 110 can be created in dependence on how, for example, a dynamic response of a gas exchange and therefore a reaction speed of the detection device 100 to changes in a composition of the measurement medium or an exhaust gas composition, in particular with respect to a concentration of the at least one gaseous analyte, is defined, predefined, or suitable. Therefore, an enclosure volume, a number of passage openings 136, and at least one dimension of the passage openings 136 can be created so that both a minimum number of particles can reach the sensor element 120 and also a suitable sensor dynamic response can be achieved. Since, for example, a minimal size of soot particles in exhaust gases is a few hundred nanometers, the diameters of the passage openings 136 or the pore size can be approximated to this minimal size of soot particles. If, in spite of active heating of the protective cap 130 or the porous cap wafer, partial pore clogging cannot be precluded over a service life, it is possible to enlarge the diffusion section 134 or a heated, porous area of the protective cap 130 by a suitable amount, so that sufficient gas permeability can still be implemented up to the end of a planned service life. Maximum dimensions of the protective cap 130 are oriented to requirements for sensor dynamic response and to a chip area of the detection device 100 which is acceptable with respect to costs and assembly and packaging technology. Exemplary dimensions of the detection device 100 comprise a width of approximately 1 mm, a height of approximately 2 mm, and a depth of approximately 1 mm. The solid electrolyte layer 126 is, for example, 100 nm to 1 μm thick. The detection device 100 reaches operational readiness in less than 3 seconds, for example. A required heating power to operating temperature is, for example, approximately 100 mW.

Figure 3:
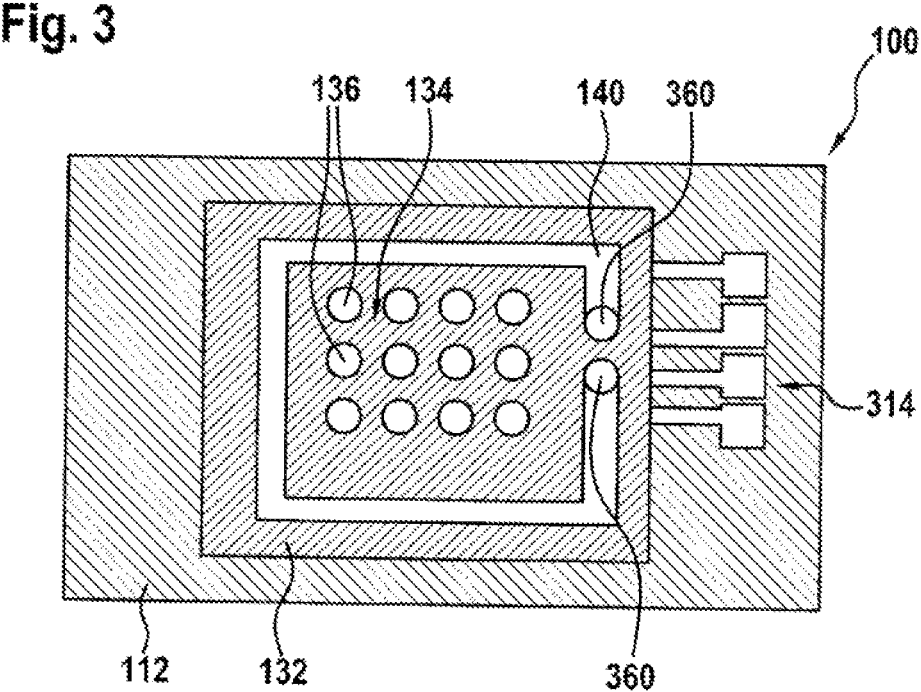
FIG. 3 shows a schematic top view of the detection device 100 from FIG. 1 to FIG. 2E.

FIG. 3 shows a schematic top view of the detection device 100 from FIG. 1 to FIG. 2E. In this case, the semiconductor substrate 112 of the detection section, the semiconductor material 132 of the protective cap, the diffusion section 134 having an exemplary number of passage openings 136 and the temperature-control unit 140 or the platinum cap heater are shown of the detection device 100 because of the view, wherein four external electrical terminals 314 of the detection device 100, solely as examples, and two contact units 360 of the detection device 100, solely as examples, are additionally shown in FIG. 3.

In this case, the external electrical terminals 314 are arranged on the semiconductor substrate 112. The external electrical terminals 314 are embodied, for example, as terminal surfaces or contact pads. Although it is not recognizable in FIG. 3 because of the view, the sensor element of the detection section is thus covered or overlaid by the protective cap. The detection section therefore comprises the semiconductor substrate 112 or a sensor wafer having two platinum levels as electrodes, a solid electrolyte membrane, and the four external electrical terminals 314 as examples.

The contact units 360 are designed to establish an electrically conductive connection between the temperature-control unit 140 and the detection section. For this purpose, the contact units 360 are created or arranged so that the contact units 360 are connected in an electrically conductive manner to both the temperature-control unit 140 and also to electrical conductor tracks or lines which are arranged in or on the semiconductor substrate 112. According to the exemplary embodiment of the present disclosure illustrated in FIG. 3, the contact units 360 are embodied as through contacts. In this case, the temperature-control unit 140 is connected by means of the two contact units 360 to two conductor tracks on the semiconductor substrate 112, which lead to two of the external electrical terminals 314.

To simplify interconnection of the temperature-control unit 140 or cap wafer heating electrode and the detection section or sensor section, the temperature-control unit 140 is connected in an electrically conductive manner to a metal layer plane on the semiconductor substrate via through contacts, so-called through silicon vias (TSV), as an alternative to a wire bonding method or a use of bond wires. To keep expenditure low with respect to a sensor interface or external contact of the detection device 100, it is possible to connect electrical contacts for the temperature-control unit 140 and means for the temperature control of the detection section in the detection device 100 or on the chip side, whereby a required number of the external electrical terminals 314, and therefore a number of costly external cable connections for the detection device 100, through the protective cap 130 or the heated cap wafer filter can be maintained. The electrical connection or interconnection of the temperature-control unit 140 and the means for temperature control of the detection section in the detection device 100 can be embodied in a series circuit or parallel circuit.

Figure 4:
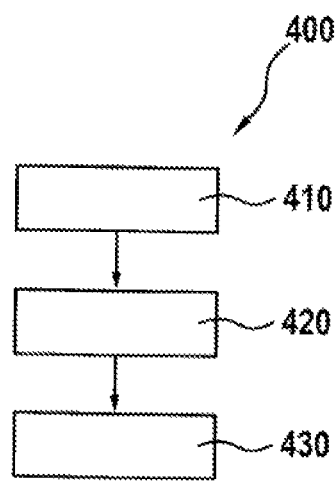
FIG. 4 shows a flow chart of a method according to one exemplary embodiment of the present disclosure.

FIG. 4 shows a flow chart of a method 400 according to one exemplary embodiment of the present disclosure. The method 400 relates to a method for producing a detection device, which can be used as already described as a device for detecting at least one gaseous analyte. By executing the method 400, a detection device like the detection device from FIG. 1 to FIG. 2E is advantageously producible. During execution of the method 400, production states are achievable, which correspond or are similar to the production states shown in FIG. 2A to FIG. 2E.

The method 400 comprises a step 410 of providing a detection section and a protective cap formed from a semiconductor material. In this case, the detection section comprises a semiconductor substrate and at least one sensor element, which is arranged on the semiconductor substrate, having two electrodes and a solid electrolyte layer arranged between the electrodes. In a subsequent step 420 of processing, the protective cap is processed, to arrange at least one temperature-control unit for temperature control of the protective cap on the protective cap and to create a diffusion section having a plurality of passage openings for the gaseous analyte at least in a partial section of the protective cap. In a step 430 of application, which can be executed subsequently in relation to the step 420 of processing, the protective cap is applied to the detection section to cover the at least one sensor element.

According to one exemplary embodiment, in the step 420 of processing, a thickness of the protective cap within the diffusion section is reduced to a lesser thickness than outside the diffusion section. According to one exemplary embodiment, in the step 420 of processing, the plurality of passage openings in the diffusion section of the protective cap are also manufactured by means of at least one micromechanical process, which comprises, for example, etching and additionally or alternatively laser drilling. According to one exemplary embodiment, in the step 430 of application, or alternatively after the step 430 of application, the at least one temperature-control unit is also connected in an electrically conductive manner to the detection section by means of at least one contact unit.

The exemplary embodiments which are described and shown in the figures are only selected as examples. Different exemplary embodiments can be combined with one another in their entirety or with respect to individual features. One exemplary embodiment can also be supplemented with features of a further exemplary embodiment. Furthermore, the method steps proposed here can be executed repeatedly and also in a sequence other than that described.

If an exemplary embodiment comprises an "and/or" linkage between a first feature and a second feature, this is to be read to mean that the exemplary embodiment according to one embodiment comprises both the first feature and also the second feature and according to a further embodiment comprises either only the first feature or only the second feature.

What is claimed is:

1. A device for detecting at least one gaseous analyte, comprising:
    a detection section including a semiconductor substrate and at least one sensor element located on the semiconductor substrate, the at least one sensor element having two electrodes and a solid electrolyte layer arranged between the two electrodes;
    a protective cap formed from a semiconductor material and configured to cover the at least one sensor element;
    at least one temperature-control unit located on the protective cap and configured for temperature control of the protective cap; and
    a diffusion section having a plurality of passage openings for the at least one gaseous analyte located at least in a partial section of the protective cap.

2. The device according to claim 1, wherein:
    the passage openings of the plurality of passage openings have main axes of extension, which extend in parallel to one another within a tolerance range, and the passage openings of the plurality of passage openings have a diameter which is adapted to a molecule size of the at least one gaseous analyte.

3. The device according to claim 1, wherein the protective cap has a lesser thickness inside the partial section than outside the partial section.

4. The device according to claim 1, wherein the protective cap is formed in a manner adapted to at least one parameter of usage surroundings of the device with respect to an area of the diffusion section and/or a volume which can be enclosed between the detection section and the protective cap, and in which the at least one sensor element is located.

5. The device according to claim 1, wherein the at least one temperature-control unit is connectable or connected in an electrically conductive manner to the detection section by at least one contact unit.

6. The device according to claim 1, wherein:
the at least one temperature-control unit is formed from a metal, and
an insulator layer made of an electrically insulating material is located between the at least one temperature-control unit and the protective cap.

7. A method for producing a device for detecting at least one gaseous analyte, comprising:
forming (i) a detection section comprising a semiconductor substrate and at least one sensor element located on the semiconductor substrate, the at least one sensor element having two electrodes and a solid electrolyte layer arranged between the two electrodes, and (ii) a protective cap formed from a semiconductor material;
processing the protective cap (i) to arrange at least one temperature-control unit for temperature control of the protective cap on the protective cap, and (ii) to create a diffusion section having a plurality of passage openings for the gaseous analyte at least in a partial section of the protective cap; and
applying the protective cap to the detection section to cover the at least one sensor element.

8. The method according to claim 7, wherein processing the protective cap further comprises:
reducing a thickness of the protective cap within the diffusion section to a lesser thickness than outside the diffusion section.

9. The method according to claim 7, wherein processing the protective cap further comprises:
manufacturing the plurality of passage openings in the diffusion section of the protective cap by at least one micromechanical process including at least one of etching and laser drilling.

10. The method according to claim 7, wherein applying the protective cap further comprises:
connecting the at least one temperature-control unit in an electrically conductive manner to the detection section with at least one contact unit.

* * * * *